United States Patent
Cui et al.

(10) Patent No.: US 12,264,119 B2
(45) Date of Patent: Apr. 1, 2025

(54) PROCESS AND DEVICE FOR CONTINUOUS FLOW SIDE-CHAIN ALKYLATION

(71) Applicant: Qingdao University of Science and Technology, Qingdao (CN)

(72) Inventors: Peizhe Cui, Qingdao (CN); Jianguang Qi, Qingdao (CN); Wenhui Xu, Qingdao (CN); Yinglong Wang, Qingdao (CN); Zhaoyou Zhu, Qingdao (CN); Kaiguang Wang, Qingdao (CN); Xin Li, Qingdao (CN); Fanqing Meng, Qingdao (CN); Limei Zhong, Qingdao (CN); Shuli Yin, Qingdao (CN); Lei Han, Qingdao (CN); Jianbo Jia, Qingdao (CN); Zhonghui Zheng, Qingdao (CN)

(73) Assignee: Qingdao University of Science and Technology, Qingdao (CN)

( * ) Notice: Subject to any disclaimer, the term of this patent is extended or adjusted under 35 U.S.C. 154(b) by 43 days.

(21) Appl. No.: 18/229,220

(22) Filed: Aug. 2, 2023

(65) Prior Publication Data
US 2023/0391686 A1    Dec. 7, 2023

(30) Foreign Application Priority Data
Jun. 2, 2022   (CN) ......................... 202210624833.X

(51) Int. Cl.
*C07C 2/54* (2006.01)
*B01J 8/00* (2006.01)
*B01J 8/08* (2006.01)

(52) U.S. Cl.
CPC ............... *C07C 2/54* (2013.01); *B01J 8/0015* (2013.01); *B01J 8/085* (2013.01); *B01J 2208/00168* (2013.01); *B01J 2208/00769* (2013.01)

(58) Field of Classification Search
CPC ......... C07C 2/54; C07C 2523/04; C07C 2/58; C07C 51/353; B01J 8/0015; B01J 8/085;
(Continued)

(56) References Cited

U.S. PATENT DOCUMENTS

| | | | | |
|---|---|---|---|---|
| 5,198,594 A | * | 3/1993 | Lillwitz | B01J 23/04 585/452 |
| 6,100,437 A | * | 8/2000 | Koehl | B01J 23/04 585/452 |

(Continued)

FOREIGN PATENT DOCUMENTS

CN       114870767 B       9/2023

OTHER PUBLICATIONS

First Office Action dated Jul. 23, 2023 for Chinese Application No. 202210624833.X (3 pages).
(Continued)

*Primary Examiner* — Ali Z Fadhel
(74) *Attorney, Agent, or Firm* — Paul D. Bianco; Fleit Intellectual Property Law

(57) ABSTRACT

A process and a device for continuous flow side-chain alkylation which relate to the technical field of organic synthesis. In this process and the device for continuous flow side-chain alkylation, an ibuprofen raw material is prepared with alkylbenzene as a raw material. This raw material alkylbenzene is easily available and has a low cost, and is suitable for scale-up production. Moreover, an entire preparation process adopts continuous chemical synthesis, and a reaction time of each stage can be precisely controlled, which is beneficial to control a total reaction time and reduce an amount of impurities produced. In this way, a purity and a yield of the ibuprofen raw material are improved. In summary, a continuous synthesis method for side-chain
(Continued)

alkylation of alkylbenzene provided by the present disclosure shows a low cost and a high yield.

2 Claims, 1 Drawing Sheet

(58) Field of Classification Search
CPC .... B01J 2208/00168; B01J 2208/00769; B01J 19/0006; B01J 4/001; B01J 2219/00006; Y02P 20/584
See application file for complete search history.

(56) References Cited

U.S. PATENT DOCUMENTS

| | | | |
|---|---|---|---|
| 2003/0023124 A1* | 1/2003 | De Stefanis | C07B 37/02 585/446 |
| 2005/0171385 A1* | 8/2005 | Jasra | C07C 45/46 568/319 |
| 2016/0046543 A1* | 2/2016 | Barve | C07C 2/72 585/453 |
| 2022/0227686 A1* | 7/2022 | Kamble | B01J 35/40 |

OTHER PUBLICATIONS

Notification to Grant Patent Right for Invention dated Sep. 1, 2023 for Chinese Application No. 202210624833.X (2 pages).

* cited by examiner

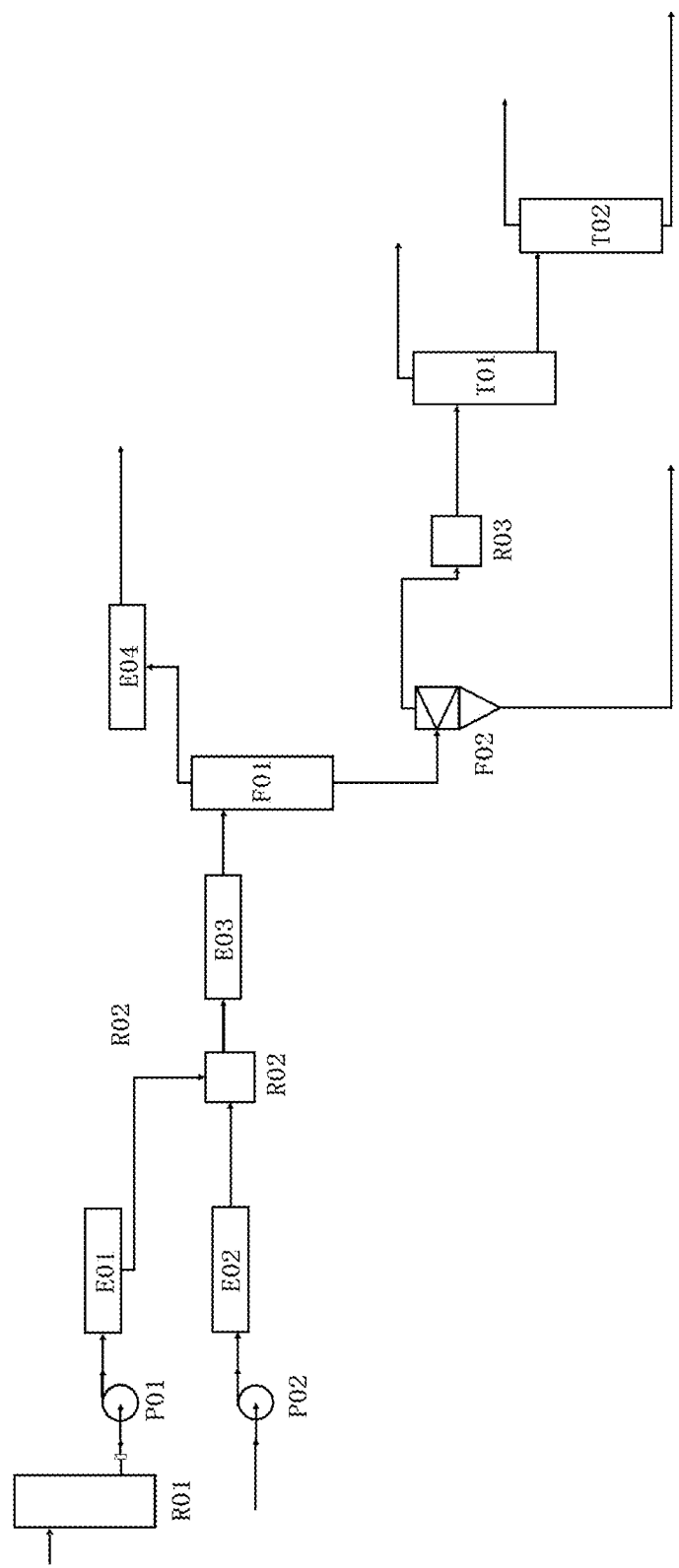

PROCESS AND DEVICE FOR CONTINUOUS FLOW SIDE-CHAIN ALKYLATION

CROSS REFERENCE TO RELATED APPLICATION

This patent application claims the benefit and priority of Chinese Patent Application No. 202210624833.X, filed with the China National Intellectual Property Administration on Jun. 2, 2022, the disclosure of which is incorporated by reference herein in its entirety as part of the present application.

TECHNICAL FIELD

The present disclosure relates to the technical field of organic synthesis, in particular to a process and a device for continuous flow side-chain alkylation.

BACKGROUND

Ibuprofen is a common antipyretic and analgesic drug, as well as a non-steroidal anti-inflammatory drug, and is widely used due to its high efficiency and low side effects in the fields of anti-inflammatory agent, analgesic, and antipyretic. At present, a production process of the ibuprofen mostly adopts aryl 1,2-transposition rearrangement. Ibuprofen is prepared through processes including acylation, condensation, rearrangement, and hydrolysis, and various intermediates need to be synthesized during the production. These intermediates are generally synthesized by side-chain alkylation of alkylbenzenes. Currently, batch reaction is generally adopted, with complex processes, unstable product quality, high energy consumption, and poor conversion rate of the raw material alkylbenzene. These deficiencies are main factors limiting the application of batch reaction in process industries.

So far, an ibuprofen raw material is mostly synthesized through a five-step reaction with an iodine catalyst or palladium catalyst and using the alkylbenzene as a raw material. This production process generally adopts a reactor-type batch reaction, which shows serious environmental pollution, high production cost, many reaction by-products, and harsh reaction conditions. Moreover, this production process requires complicated waste treatment in the later stage. As a result, the production process is not suitable for large-scale production.

SUMMARY

In order to solve the above technical problems, an objective of the present disclosure is to provide a novel method for continuous synthesis based on side-chain alkylation of alkylbenzene, so as to achieve efficient and safe production of an ibuprofen raw material. At the same time, the ibuprofen raw material produced has stable quality and high purity. The method shows less side reactions, reduced waste recovery difficulty, low energy consumption, and simple process.

To achieve the above objective, the present disclosure provides the following technical solutions.

The present disclosure provides a process and a device for continuous flow side-chain alkylation. The process includes the following steps: transporting alkylbenzene into a catalyst synthesis reactor; mixing a carrier inorganic substance and an alkali metal catalyst uniformly to obtain a raw material A; using an alkene as a raw material B;

synthesizing a catalyst in the catalyst synthesis reactor using the raw material A, and transporting the catalyst and the alkylbenzene simultaneously into an alkylbenzene preheater to allow preheating;

preheating the raw material B in an alkene preheater;

mixing an obtained preheated raw material A and an obtained preheated raw material B in a gas-liquid mixer to obtain a mixed solution;

transporting the mixed solution as a reaction system into a double-chamber coil reactor to allow a continuous reaction to obtain an ibuprofen raw material;

cooling the reaction system after the continuous reaction is completed, separating unreacted alkene after the cooling is completed to obtain a remaining part, and recycling cooled alkene to allow secondary utilization; separating and recycling a solid catalyst from the remaining part to obtain a remaining reaction liquid, and introducing the remaining reaction liquid and a quencher into a quenching tank to allow quenching, such that a residual catalyst and other active substances are quenched; and subjecting a system obtained after the quenching to continuous extraction with water as an extractant to transfer impurities into an aqueous phase, and separating remaining alkylbenzene and ibuprofen raw material by extraction with dimethyl sulfoxide (DMSO), where a separation yield is 85 wt %.

Optionally, the catalyst synthesis reactor works at 80° C. to 200° C. and a pressure of 2 MPa to 5 MPa.

Optionally, the alkylbenzene preheater works at 150° C. to 300° C. and a pressure of 5 MPa to 15 MPa.

Optionally, the alkene preheater works at 150° C. to 300° C. and a pressure of 5 MPa to 15 MPa.

Optionally, the mixed solution is subjected to the continuous reaction for 10 min.

Optionally, the quencher is a 10 wt % NaOH aqueous solution.

Optionally, the quenching is conducted at less than or equal to 30° C.

Optionally, the cooled alkene is recycled to allow secondary utilization at 20° C.

The present disclosure further provides a device for continuous flow side-chain alkylation, including a catalyst synthesis reactor, a first transfer pump, a second transfer pump, an alkylbenzene preheater, an alkene preheater, a double-chamber coil reactor, a first cooler, a gas-liquid separator, a second cooler, a hydrocyclone, a quenching tank, a pre-extraction tower, and an extraction tower; where the catalyst synthesis reactor is in communication with the alkylbenzene preheater through the first transfer pump; an outlet of the second transfer pump is in communication with the alkene preheater; the alkylbenzene preheater and the alkene preheater each are in communication with the double-chamber coil reactor, and the double-chamber coil reactor is in communication with the gas-liquid separator through the first cooler; a gas outlet of the gas-liquid separator is in communication with the second cooler, a liquid outlet of the gas-liquid separator is in communication with the hydrocyclone, and the pre-extraction tower and the quenching tank are arranged between the hydrocyclone and the extraction tower.

Compared with the prior art, the present disclosure has the following technical effects:

In the process and the device for continuous flow side-chain alkylation of the present disclosure, an ibuprofen raw material is prepared with alkylbenzene as a raw material. This raw material is easily available and has a low cost, and is suitable for scale-up production. Moreover, an entire preparation process adopts continuous chemical synthesis, and a reaction time of each stage can be precisely controlled, which is beneficial to control a total reaction time and reduce an amount of impurities produced. In this way, a purity and a yield of the ibuprofen raw material are improved. In summary, a continuous synthesis method for side-chain alkylation of alkylbenzene provided by the present disclosure shows a low cost and a high yield.

BRIEF DESCRIPTION OF THE DRAWING

To describe the technical solutions in embodiments of the present disclosure or in the prior art more clearly, the accompanying drawing required for the embodiments is briefly described below. Apparently, the accompanying drawing in the following description show merely some embodiments of the present disclosure, and those of ordinary skill in the art may still derive other accompanying drawing from this accompanying drawing without creative efforts.

The sole FIGURE shows a process flow chart of a novel process for continuous flow side-chain alkylation of the present disclosure; where in the FIGURE, R01—catalyst synthesis reactor, P01—first transfer pump, P02—second transfer pump, E01—alkylbenzene preheater, E02—alkene preheater, R02—double-chamber coil reactor, E03—first cooler, F01—gas-liquid separator, E04—second cooler, F02—hydrocyclone, R03—quenching tank, T01—pre-extraction tower, and T02—extraction tower.

DETAILED DESCRIPTION OF THE EMBODIMENTS

The technical solutions of the embodiments of the present disclosure are clearly and completely described below with reference to the drawings in the embodiments of the present disclosure. Apparently, the described embodiments are merely a part rather than all of the embodiments of the present disclosure. All other embodiments obtained by those skilled in the art based on the embodiments of the present disclosure without creative efforts shall fall within the protection scope of the present disclosure.

Example 1

Alkylbenzene (80 g/s) was transported into a catalyst synthesis reactor R01; a carrier inorganic substance (15 g/s) and an alkali metal catalyst (5 g/s) were mixed uniformly to obtain a raw material A. An alkene (50 g/s) was used as a raw material B.

As shown in the sole FIGURE, a continuous reaction device was installed and debugged. The raw material A and the raw material B were connected to the catalyst synthesis reactor R01 and an alkene preheater E02 in sequence, and a flow rate was automatically controlled by an automatic feeding system. A catalyst was synthesized in the catalyst synthesis reactor R01 using the raw material A (100° C., 3 MPa), and the catalyst and the alkylbenzene were transported simultaneously into an alkylbenzene preheater E01 to allow preheating (200° C., 7 MPa). The raw material B was preheated in the alkene preheater E02 (200° C., 7 MPa). An obtained preheated raw material A and an obtained preheated raw material B were mixed in a gas-liquid mixer to obtain a mixed solution.

The mixed solution as a reaction system was transported into a double-chamber coil reactor R02 of the continuous reaction device to allow a continuous reaction for 10 min to obtain an ibuprofen raw material.

After the continuous reaction was completed, the reaction system was transported into a cooler to allow cooling, and unreacted alkene was separated after the cooling, and the alkene was cooled to 20° C. by the cooler and then recycled to the reaction section for secondary utilization. A remaining material entered a hydrocyclone F02 for separation to obtain a solid catalyst, which was recycled to the reaction section for utilization; a remaining reaction liquid and a quencher (a 10 wt % NaOH aqueous solution) simultaneously flowed into a quenching device (constant-stirring tank reactor) for quenching at less than 30° C.

A system obtained after the quenching was introduced into an extraction device (continuous extraction tower) and subjected to continuous extraction with water as an extractant (4 mL/g) to transfer impurities into an aqueous phase, and remaining alkylbenzene and ibuprofen raw material were separated by extraction with DMSO (8 mL/g), where a separation yield was 85 wt %.

Example 2

Alkylbenzene (50 g/s) was transported into a catalyst synthesis reactor R01; a carrier inorganic substance (10 g/s) and an alkali metal catalyst (2 g/s) were mixed uniformly to obtain a raw material A. An alkene (30 g/s) was used as a raw material B.

As shown in the sole FIGURE, a continuous reaction device was installed and debugged. The raw material A and the raw material B were connected to the catalyst synthesis reactor R01 and an alkene preheater E02 in sequence, and a flow rate was automatically controlled by an automatic feeding system. A catalyst was synthesized in the catalyst synthesis reactor R01 using the raw material A (150° C., 3 MPa), and the catalyst and the alkylbenzene were transported simultaneously into an alkylbenzene preheater E01 to allow preheating (250° C., 10 MPa). The raw material B was preheated in the alkene preheater E02 (250° C., 10 MPa). An obtained preheated raw material A and an obtained preheated raw material B were mixed in a gas-liquid mixer to obtain a mixed solution.

The mixed solution as a reaction system was transported into a double-chamber coil reactor R02 of the continuous reaction device to allow a continuous reaction for 15 min to obtain an ibuprofen raw material.

After the continuous reaction was completed, the reaction system was transported into a cooler to allow cooling, and unreacted alkene was separated after the cooling, and the alkene was cooled to 20° C. by the cooler and then recycled to the reaction section for secondary utilization. A remaining material entered a hydrocyclone F02 for separation to obtain a solid catalyst, which was recycled to the reaction section for utilization; a reaction liquid and a quencher (a 10 wt % NaOH aqueous solution) simultaneously flowed into a quenching device (constant-stirring tank reactor) for quenching at less than 30° C.

A system obtained after the quenching was introduced into an extraction device (continuous extraction tower) and subjected to continuous extraction with water as an extractant (3 mL/g) to transfer impurities into an aqueous phase, and remaining alkylbenzene and ibuprofen raw material were separated by extraction with DMSO (6 mL/g), where a separation yield was 83 wt %.

Example 3

As shown in the sole FIGURE, the present disclosure further provided a device for continuous flow side-chain alkylation, including a catalyst synthesis reactor R01, a first transfer pump P01, a second transfer pump P012, an alkylbenzene preheater E01, an alkene preheater E02, a double-chamber coil reactor R02, a first cooler E03, a gas-liquid separator F01, a second cooler E04, a hydrocyclone F02, a pre-extraction tower T01, and an extraction tower T02. The catalyst synthesis reactor R01 was in communication with the alkylbenzene preheater E01 through the first transfer pump P01; an outlet of the second transfer pump P012 was in communication with the alkene preheater E02; the alkylbenzene preheater E01 and the alkene preheater E02 each were in communication with the double-chamber coil reactor R02, and the double-chamber coil reactor R02 was in communication with the gas-liquid separator F01 through the first cooler E03; a gas outlet of the gas-liquid separator F01 was in communication with the second cooler E04, a liquid outlet of the gas-liquid separator F01 was in communication with the hydrocyclone F02, and the pre-extraction tower T01 was arranged between the hydrocyclone F02 and the extraction tower T02.

The catalyst synthesis reactor R01 was configured to uniformly mix the alkylbenzene, carrier inorganic substance, and alkali metal catalyst to prepare the raw material A. The first transfer pump P01 was configured to transport the raw material A to the alkylbenzene preheater E01 for preheating, and the second transfer pump P012 was configured to transport the raw material B to the alkene preheater E02 for preheating. The double-chamber coil reactor R02 was configured to conduct the continuous reaction of the raw material A and raw material B. The first cooler E03 was configured to cool a reaction system obtained after the continuous reaction, the gas-liquid separator F01 was configured to separate unreacted alkene, and the second cooler E04 was configured to cool the separated unreacted alkene. The hydrocyclone F02 was configured to separate the solid catalyst.

It should be noted that it is obvious to those skilled in the art that the present disclosure is not limited to the details of the above exemplary embodiments, and that the present disclosure can be implemented in other specific forms without departing from the spirit or basic features of the present disclosure. Therefore, the embodiments should be regarded as exemplary and non-limiting in every respect. The scope of the present disclosure is defined by the appended claims rather than the above description, therefore, all changes falling within the meaning and scope of equivalent elements of the claims should be included in the present disclosure, and any reference numerals in the claims should not be construed as a limitation to the claims involved.

Specific examples are used in this description for illustration of the principles and embodiments of the present disclosure. The foregoing description is just meant to help understand the method of the present disclosure and its core idea. In addition, various modifications can be made by a person skilled in the art to the specific embodiments and the application scope in accordance with the idea of the present disclosure. In conclusion, the content of the description shall not be construed as limitations to the present disclosure.

What is claimed is:

1. A process for continuous flow side-chain alkylation, comprising the following steps:
   transporting alkylbenzene into a catalyst synthesis reactor; mixing a carrier inorganic substance and an alkali metal catalyst uniformly to obtain a raw material A; using an alkene as a raw material B;
   synthesizing a catalyst in the catalyst synthesis reactor using the raw material A, and transporting the catalyst and the alkylbenzene simultaneously into an alkylbenzene preheater to allow preheating;
   preheating the raw material B in an alkene preheater;
   mixing an obtained preheated raw material A and an obtained preheated raw material B in a gas-liquid mixer to obtain a mixed solution;
   transporting the mixed solution as a reaction system into a double-chamber coil reactor to allow a continuous reaction to obtain an ibuprofen raw material;
   cooling the reaction system after the continuous reaction is completed, separating unreacted alkene after the cooling is completed to obtain a remaining part, and recycling cooled alkene to allow secondary utilization; separating and recycling a solid catalyst from the remaining part to obtain a remaining reaction liquid, and introducing the remaining reaction liquid and a quencher into a quenching tank to allow quenching; and
   subjecting a system obtained after the quenching to continuous extraction with water as an extractant to transfer impurities into an aqueous phase, and separating remaining alkylbenzene and ibuprofen raw material by extraction with dimethyl sulfoxide (DMSO), wherein a separation yield is 85 wt %;
   the catalyst synthesis reactor works at 80° C. to 200° C. and a pressure of 2 MPa to 5 MPa;
   the alkylbenzene preheater works at 150° C. to 300° C. and a pressure of 5 MPa to 15 MPa;
   the alkene preheater works at 150° C. to 300° C. and a pressure of 5 MPa to 15 MPa;
   the mixed solution is subjected to the continuous reaction for 10 min;
   the quencher is a 10 wt % NaOH aqueous solution;
   the quenching is conducted at less than or equal to 30° C.; and
   the cooled alkene is recycled for reutilization at 20° C.

2. A device for continuous flow side-chain alkylation based on the process for continuous flow side-chain alkylation according to claim 1, comprising a catalyst synthesis reactor, a first transfer pump, a second transfer pump, an alkylbenzene preheater, an alkene preheater, a double-chamber coil reactor, a first cooler, a gas-liquid separator, a second cooler, a hydrocyclone, a quenching tank, a pre-extraction tower, and an extraction tower; wherein the catalyst synthesis reactor is in communication with the alkylbenzene preheater through the first transfer pump; an outlet of the second transfer pump is in communication with the alkene preheater; the alkylbenzene preheater and the alkene preheater each are in communication with the double-chamber coil reactor, and the double-chamber coil reactor is in communication with the gas-liquid separator through the first cooler; a gas outlet of the gas-liquid separator is in communication with the second cooler, a liquid outlet of the gas-liquid separator is in communication with the hydrocyclone, and the pre-extraction tower and the quenching tank are arranged between the hydrocyclone and the extraction tower.

* * * * *